(12) United States Patent
Su et al.

(10) Patent No.: US 8,674,020 B2
(45) Date of Patent: Mar. 18, 2014

(54) PROCESS FOR PREPARING POLYAMIDES (75) Inventors: Wu Su, Leicester (GB); Glenn Ashley Burley, Leicester (GB)

(73) Assignee: University of Leicester, Leicester (GB)

( * ) Notice: Subject to any disclaimer, the term of this patent is extended or adjusted under 35 U.S.C. 154(b) by 0 days.

(21) Appl. No.: 13/266,765

(22) PCT Filed: Apr. 28, 2010

(86) PCT No.: PCT/GB2010/050687
§ 371 (c)(1),
(2), (4) Date: Jan. 20, 2012

(87) PCT Pub. No.: WO2010/125382
PCT Pub. Date: Nov. 4, 2010

(65) Prior Publication Data
US 2012/0130017 A1    May 24, 2012

(30) Foreign Application Priority Data

Apr. 28, 2009 (GB) .................................. 0907249.7

(51) Int. Cl.
C07K 1/04 (2006.01)
C08F 283/00 (2006.01)
C08G 63/48 (2006.01)
C08G 63/91 (2006.01)
A61K 38/00 (2006.01)
C07K 2/00 (2006.01)
C07K 4/00 (2006.01)
C07K 5/00 (2006.01)
C07K 7/00 (2006.01)
C07K 14/00 (2006.01)
C07K 16/00 (2006.01)
C07K 17/00 (2006.01)
A61K 38/12 (2006.01)

(52) U.S. Cl.
USPC ......... 525/54.11; 530/337; 530/321; 530/300

(58) Field of Classification Search
None
See application file for complete search history.

(56) References Cited

U.S. PATENT DOCUMENTS 6,673,940 B1   1/2004  Dervan et al.
7,067,622 B2   6/2006  Sugiyama et al.

FOREIGN PATENT DOCUMENTS

WO    WO 00/02898         1/2000
WO    WO 00/02898 A1      1/2000
WO    WO 0002898 A1 *     1/2000

OTHER PUBLICATIONS

Rojas et al "Evaluation of Automated Synthesis for Chain and Step Growth Polymerizations: Can Robots Replace the Chemists?" J Polymer Sci Part A 47:49-58. Published Jan. 1, 2009.*
Cho, et al., "Cyclic polyamides for recognition in the minor groove of DNA," *Proc. Natl. Acad. Sci. USA* (1995) 92:10389-10392.
Edelson, et al., "Influence of structural variation on nuclear localization of DNA-binding polyamide-fluorophore conjugates," *Nucleic Acids Research* (2004) 32(9): 2802-2818.

(Continued)

*Primary Examiner* — Cecilia J Tsang
*Assistant Examiner* — Zachary J Miknis
(74) *Attorney, Agent, or Firm* — Knobbe Martens Olson & Bear LLP (57) ABSTRACT

There is provided a novel process for preparing polyamides (in particular cyclic and hairpin polyamides) comprising the step of coupling an amine with a Boc-protected amino acid monomer in the presence of diphosgene and/or triphosgene. Such a process may be performed on a solid or solution phase.

16 Claims, 6 Drawing Sheets

Synthesis of cyclic peptide by an aryl hydrazide linker resin

(56) References Cited

OTHER PUBLICATIONS

Weiss, et al., "Recognizing and exploiting differences between RNAi and small-molecule inhibitors," *Nat. Chem. Biol.* (2007) 3(12): 739-744.

Cho et al, Cyclic Polyamides for Recognition in the Minor Groove of DNA, Proceedings of the National Academy of Sciences of the United States, Oct. 1995, pp. 10389-10392, vol. 92, USA.

PCT, International Search Report and Written Opinion, May 23, 2011, for International Application No. PCT/GB2010/050687.

Baird, Eldon E. et al., Solid Phase Synthesis of Polyamides Containing Imidazole and Pyrrole Amino Acids, J. Am. Chem. Soc., 1996, pp. 6141-6146, vol. 118, American Chemical Society.

Bando, Toshikazu et al., Synthesis and Biological Properties of Sequence-Specific DNA-Alkylating Pyrrole-Imidazole Polyamides, Accounts of Chemical Research, 2006, pp. 935-944, vol. 39, No. 12, American Chemical Society.

Cohen, Justin D. et al., Addressing Single Molecules on DNA Nanostructures, Angew. Chem. Int. Ed., 2007, pp. 7956-7959, vol. 46, Wiley-VCH Verlag GmbH & Co., Weinheim, Germany.

Cohen, Justin D. et al., Programming Multiple Protein Patterns on a Single DNA Nanostructure, J. Am. Chem. Soc., 2008, pp. 402-403, vol. 130, American Chemical Society.

Dervan, Peter B. et al., Recognition of the DNA Minor Groove by Pyrrole-Imidazole Polyamides, Current Opinion in Structural Biology, 2003, pp. 284-299, vol. 13, Elsevier.

Dillon, Christopher P. et al., RNAi as an Experimental and Therapeutic Tool to Study and Regulate Physiological and Disease Processes, Annu. Rev. Physiol., 2005, pp. 147-173, vol. 67, Annual Reviews.

Dose, Christian et al., Next Generation Hairpin Polyamides with (R)-3,4-Diaminobutyric Acid Turn Unit, J. Am. Chem. Soc., 2008, pp. 6859-6866, vol. 130, No. 21, American Chemical Society.

Kim, Daniel H. et al., Strategies for Silencing Human Disease Using RNA Interference, Nature Reviews Genetics, Mar. 2007, pp. 173-184, vol. 8, Nature Publishing Group.

Krutzik, Peter O. et al., Rapid Solid-Phase Synthesis of DNA-Binding Pyrrole-Imidazole Polyamides, Bioorganic & Medicinal Chemistry Letters, 2002, pp. 2129-2132, vol. 12, Elsevier Science Ltd.

Thern, Bernd et al., Triphosgene as Highly Efficient Reagent for the Solid-Phase Coupling of N-alkylated Amino Acids—Total Synthesis of Cyclosporin O, Tetrahedron Letters, 2002, pp. 5013-5016, vol. 43, Elsevier Science Ltd.

Thern, Bernd et al., Total Synthesis of the Nematicidal Cyclododecapeptide Omphalotin A by Using Racemization-Free Triphosgene—Mediated Couplings in the Solid Phase, Angew. Chem. Int. Ed., 2002, pp. 2307-2309, vol. 41, No. 13, Wiley-VCH Verlag GmbH, Weinheim, Germany.

Wurtz, Nicholas R. et al., Fmoc Solid Phase Synthesis of Polyamides Containing Pyrrole and Imidazole Amino Acids, Organic Letters, 2001, pp. 1201-1203, vol. 3, No. 8, American Chemical Society.

Sewald, Norbert, "Efficient, Racemization-Free Peptide Coupling of N-Alkyl Amino Acids by Using Amino Acid Chlorides Generated In Situ—Total Syntheses of the Cyclopeptides Cyclosporin O and Omphalotin A", *Angew. Chem. Int. Ed.* (2002) 41, No. 24 p. 4661-4663.

\* cited by examiner

Figure 1: Characterisation of polyamide sequence 1

Figure 2: Characterisation of polyamide sequence 3

Figure 3: HPL chromatogram of the coupling reaction between 1 (13.2 min.) and 2 to afford product 3 (14.6 min.), Example E

FIGURE 4

FIGURE 5. Synthesis of Py-Im polyamide on PAM resin

FIGURE 6. Synthesis of cyclic peptide by an aryl hydrazide linker resin

PROCESS FOR PREPARING POLYAMIDES

CROSS-REFERENCE TO RELATED APPLICATIONS

This application is the U.S. National Phase under 35 U.S.C. §371 of International Application No. PCT/GB2010/050687 entitled NEW PROCESS AND NEW COMPOUNDS, filed Apr. 28, 2010 and published in English on Nov. 4, 2010 as WO 2010/125382, which claims priority to Great Britain Patent Application No. GB 0907249.7, filed Apr. 28, 2009.

The present invention relates to a new process for preparing polyamides (such as hairpin and cyclic polyamides), some of which polyamides themselves are new.

The ability to modulate the expression of any gene is one of the key goals in molecular medicine. Methods such as RNA interference (RNAi) provide the means to silence specific gene expression, however RNAi still poses challenges both as a research tool and as a therapeutic strategy (see: W. A. Weiss, et al., *Nat Chem Biol* 2007, 3, 739; D. H. Kim, J. J. Rossi, *Nature Reviews Genetics* 2007, 8, 173; and C. P. Dillon, et al, *Annual Review of Physiology* 2005, 67, 147).

Pyrrole-Imidazole (Py-Im) polyamides are cell-permeable synthetic ligands which can be programmed to bind to pre-determined sequences of DNA with affinities and specificities that equal or exceed natural eukaryotic transcriptional regulatory proteins. Polyamide ligands provide an alternative small molecule strategy to RNAi by binding within the minor groove of DNA and blocking gene transcription (see: P. B. Dervan, B. S. Edelson, *Current Opinion in Structural Biology* 2003, 13, 284; and T. Bando, H. Sugiyama, *Accounts of Chemical Research* 2006, 39, 935).

Specificity is achieved according to a series of base pairing rules where an anti-parallel arrangement of Py-Py building blocks bind preferentially to A,T base pairs whereas an Im-Py arrangement preferentially targets G•C over C•G, A•T or T•A base pairs.

Over one hundred analogues of polyamides (see B. S. Edelson, et al., *Nucleic Acids Research* 2004, 32, 2802) have been prepared by solid phase synthesis methodologies (see: E. E. Baird, P. B. Dervan, *Journal of the American Chemical Society* 1996, 118, 6141; N. R. Wurtz, et al., *Organic Letters* 2001, 3, 1201; Japan Science and Technology Agency, 2006; and P. O. Krutzik, A. R. Chamberlin, *Bioorganic & Medicinal Chemistry Letters* 2002, 12, 2129) which has enabled their utilization in areas ranging from biology through to nanotechnology (see J. D. Cohen, et al, *Angewandte Chemie-International Edition* 2007, 46, 7956; J. D. Cohen, et al., *Journal of the American Chemical Society* 2008, 130, 402; and C. Dose, et al., *Angewandte Chemie-International Edition* 2007, 46, 8384) yet despite their growing utility there is still no generally applicable method for the efficient preparation of collections of polyamides in high yield and purity.

Traditional solid phase synthetic protocols of polyamides have focused on the utilization of activated benzotriazole esters. These methods proceed well for resin-bound aliphatic and Py amine couplings with BocPyOH and BocImOH, however as a consequence of their lower inherent nucleophilicity, the coupling efficiencies of resin bound aminoimidazoles are significantly reduced, particularly coupled with BocPyOH.

Jung et al. reported the Fmoc-mediated synthesis of cyclic peptides containing sterically hindered secondary amines on a solid support in which triphosgene [bis(trichloromethyl) carbonate, BTC] was used as the coupling agent (see in particular B. Them, et al., *Angewandte Chemie-International Edition* 2002, 41, 2307, and B. Them, et al, *Tetrahedron Letters* 2002, 43, PII S0040).

However, given the potential utility of polyamides (in particular hairpin and cyclic polyamides), there is a need to provide alternative and/or improved processes for the preparation thereof, particularly processes that are amendable to solid or solution phase synthesis.

The listing or discussion of an apparently prior-published document in this specification should not necessarily be taken as an acknowledgement that the document is part of the state of the art or is common general knowledge.

According to the present invention, there is provided a process for the preparation of an amide linkage between an amine and the carboxylic acid of an amino-protected amino acid, which comprises a coupling reaction of an amine with an amino acid of formula I, $$PG^1\text{-HN-}A^1\text{-COOH} \qquad \qquad I$$

wherein:

$A^1$ represents an optionally substituted aliphatic or aromatic moiety;

$PG^1$ represents an amino protecting group of the formula —C(O)OR$^1$; and $R^1$ represents a secondary or tertiary $C_{3-8}$ alkyl group, characterised in that the reaction is performed in the presence of diphosgene and/or triphosgene.

According to another aspect of the invention, there is provided a process for the preparation of a polyamide of formula IG, $$X^1\text{—(—HN-}A^1\text{-CO—)}_n\text{NH—B}^1 \qquad \qquad IG$$

wherein $B^1$ represents an optionally substituted aliphatic or aromatic moiety, $X^1$ represents —PG$^1$, —H (if any protecting group has been removed), or —C(O)A$^1$, n represents an integer of one or more, and PG$^1$ and each A$^1$ is as defined above, which comprises a process as defined above.

According to a further aspect of the invention, there is provided a process for the preparation of a cyclic polyamide of formula III,

III in which n is as defined in, and each A$^1$ is independently as defined above, which comprises a process as defined above.

Preferably, in a first step, a compound of formula II, $$H_2N\text{—B}^1 \qquad \qquad II$$

is reacted with a compound of formula I as defined above, and in a subsequent step the deprotected amine so formed is further reacted with another compound of formula I, the latter step being repeated until the desired number of monomer units in the compound of formula IG is attained, wherein each step is performed in accordance with the process defined above.

Conveniently, in a first step, a compound of formula IV, $$E^1\text{-N(H)—NH}_2 \qquad \qquad IV$$

wherein $E^1$ represents an optionally substituted aliphatic or aromatic moiety, is reacted with a compound of formula I as defined above, and in a subsequent step the deprotected amine so formed is further reacted with another compound of formula I, the latter step being repeated until the desired number of monomer units in the compound of formula III is attained, thereby forming a compound of formula V, PG$^1$-(—HN-A$^1$-CO—)$_n$N(H)—N(H)-E$^1$     V which following deprotection (to remove PG$^1$), and oxidation form the corresponding compound of formula VI, H—(—HN-A$^1$-CO—)$_n$N=N-E$^1$     VI which in turn undergoes an intramolecular cyclisation reaction with concomitant cleavage of the —N=N-E$^1$ moiety.

Advantageously, either B$^1$ or E$^1$ is attached to a resin, thereby making the processes amenable to solid phase synthesis. However, it will be appreciated that the processes may also be amenable to solution phase synthesis. Hence, at least portions of the polyamide may be made by a solution phase synthesis.

Preferably, each A$^1$ independently represents —CH$_2$—CH$_2$—C(—NH$_2$)(H)—, or one of the following substructures:

Conveniently, B$^1$ represents —C(O)—CH$_2$—CH$_2$—NH$_2$ and/or E$^1$ represents phenyl.

Advantageously, the process is performed in the presence of triphosgene.

Preferably, the process is performed below about 50° C., more preferably below about 30° C., most preferably at about 20 to 25° C. Conveniently, the coupling reaction is automated. Advantageously, the process is for the production of a polyamide, such as a straight-chain polyamide, cyclic amide and hairpin polyamide. Preferably, the amino acid of formula I is comprises a natural amino acid residue or a non-natural amino acid residue, preferably a non-natural amino acid residue.

According to another aspect of the invention, there is provided a compound of formula III as defined above, wherein the compound carries at least two groups each capable of bearing a charge, preferably a positive charge.

According to a further aspect of the invention, there is provided the use of a compound prepared by a process defined above, or, of a compound of formula III as defined above for binding to a pre-determined sequence of DNA.

According to another aspect, there is provided a conjugate comprising a compound prepared by a process defined above, or, of a compound of formula III as defined above, bound to DNA.

The compound prepared by a process defined above, or, the compound of formula III may be bound to a pre-determined sequence of DNA to form the conjugate. The conjugate may be used for a variety of purposes, for example the identification of target sequences of using polyamide recognition rules. The DNA portion of the conjugate could be used for signal output via the recognition of the DNA sequence using fluorescently tagged DNA or a DNA molecular beacon.

All of the features described herein (including any accompanying claims, abstract and drawings), and/or all of the steps of any method or process so disclosed, may be combined with any of the above aspects in any combination, except combinations where at least some of such features and/or steps are mutually exclusive.

The present invention will now be described, by way of example, with reference to the accompanying figures, in which.

There is now provided a process for the preparation of an amide linkage between an amine and the carboxylic acid of a amino-protected amino acid, which comprises a coupling reaction of an amine with an amino-acid of formula I, PG$^1$-HN-A$^1$-COOH     I wherein:
A$^1$ represents an optionally substituted aliphatic or aromatic (including heteroaromatic) moiety;
PG$^1$ represents an amino protecting group of the formula —C(O)OR$^1$ (i.e. the requisite —NH$_2$ moiety of the amino acid is protected to form a —N(H)—C(O)OR$^1$ moiety) and
R$^1$ represents a secondary or tertiary C$_{3-8}$ alkyl group,
characterised in that the reaction is performed in the presence of diphosgene and/or triphosgene, which process is hereinafter referred to as "the process of the invention".

The process of the invention may be performed employing salts, solvates or protected derivatives. Hence, compounds that may be produced by the process of the invention may or may not be produced in the form of a (e.g. corresponding) salt or solvate, or a protected derivative thereof.

Compounds employed in or produced by the processes described herein (i.e. those involving the process of the invention) may exhibit tautomerism. The process of the invention therefore encompasses the use or production of such compounds in any of their tautomeric forms, or in mixtures of any such forms. The invention also encompasses the use of building blocks of the compounds defined herein, such as dimers, trimers or tetramers, which may be prepared either by solution or solid phase methods.

Similarly, the compounds employed in or produced by the processes described herein (i.e. those involving the process of the invention) may also contain one or more asymmetric atoms (e.g. carbon atoms) and may therefore exist as enantiomers or diastereoisomers, and may exhibit optical activity. The process of the invention thus encompasses the use or production of such compounds in any of their optical or diastereoisomeric forms, or in mixtures of any such forms.

Further, the compounds employed in or produced by the processes described herein may contain double bonds and may thus exist as E (entgegen) and Z (zusammen) geometric isomers about each individual double bond. All such isomers and mixtures thereof are included within the scope of the invention.

Triphosgene is the compound of chemical formula $Cl_3C-O-C(O)-OCCl_3$ (bis(trichloromethyl)carbonate; also referred to herein as BTC). It is indicated that the process of the invention is preferably performed in the presence of triphosgene. By this we mean that there is at least some triphosgene present (to activate any carboxylic acid functional group present), but there may be other coupling reagents and/or activating agents present. However, preferably, triphosgene consists of at least 50%, 60%, 70%, 80% or 85% (e.g. at least 90%) of the coupling reagents and/or activating agents employed in the process of the invention. Most preferably, the coupling reagents and/or activating agents consists exclusively (i.e. greater than 95%, preferably 99%) of triphosgene.

The use of triphosgene is preferred over the use of diphosgene.

Diphosgene is the compound of chemical formula $Cl-C(O)-OCCl_3$ (trichloromethyl chloroformate). It is indicated that the process of the invention may be performed in the presence of diphosgene. By this we mean that there is at least some diphosgene present (to activate any carboxylic acid functional group present), but there may be other coupling reagents and/or activating agents present. However, preferably, diphosgene consists of at least 50%, 60%, 70%, 80% or 85% (e.g. at least 90%) of the coupling reagents and/or activating agents employed in the process of the invention. Most preferably, the coupling reagents and/or activating agents consists exclusively (i.e. greater than 95%, preferably 99%) of diphosgene.

In the process of the invention, it is preferred that less than one molar equivalent of the diphosgene and/or triphosgene (as compared to the amine is employed). For example, a slight deficit, such as from about 0.1 to about 0.8, more preferably from about 0.2 to about 0.5, even more preferably from about 0.3 to about 0.35, most preferably about 0.33 molar equivalents, may be used. It is preferred that the temperature of the process of the invention is not raised significantly above room temperature (that is it is preferably kept below 50° C., especially, below 30° C., more preferably at about 20 to 25° C.). Preferably, the activation of a carboxylic acid group by reaction in the presence of triphosgene is performed at, or below, room temperature. Unexpectedly and advantageously, this may lead to the process of the invention being more efficient and resulting in higher yields.

It is stated that an amine is employed to the process of the invention. For the purposes of this invention, by this we mean any compound containing a $-NH_2$ moiety, including a $-NH_2$ moiety attached to a carbon atom, as well as a $-NH_2$ moiety attached to a heteroatom (e.g. nitrogen; so forming for example, a hydrazide functional group, i.e. $-N(H)-NH_2$). Furthermore, such a compound containing the $-NH_2$ moiety may be an amino acid, or a compound containing an amino acid monomer unit, e.g. one that may be prepared by the process(es) of the invention described herein.

The process of the invention proceeds in the presence of a compound of formula I that is an amino acid, in which the amino moiety is protected. The compound formed by the process of the invention depends on the amine reagent that is employed, i.e. the process of the invention produces a moiety of formula IA, $PG^1\text{-HN-}A^1\text{-CONH}-$  IA wherein $A^1$ and $PG^1$ are as hereinbefore defined. When the amine employed in the process of the invention it may be represented by a compound of formula II, $H_2N-B^1$  II wherein $B^1$ represents an optionally substituted aliphatic or aromatic moiety, in which case the compound formed by the process of the invention is a compound of formula IB, $PG^1\text{-HN-}A^1\text{-CONH}-B^1$  IB wherein $B^1$ is as hereinbefore defined. However, the amine employed in the process of the invention may also be (the amino moiety of):
an amino acid (e.g. in which the carboxylic acid moiety is protected); or, preferably,
an amino amide (i.e. an amino acid in which the carboxylic acid has been coupled with an amine, for example an unprotected compound of formula IB, i.e. a compound of formula ID as described hereinafter); or
a polyamide (i.e. a compound containing at least two amide monomers, e.g. which may be formed by reaction of a compound of formula ID, as defined hereinafter, and a compound of formula I as hereinbefore defined, i.e. a compound of formula IF as defined hereinafter).

The moiety of formula IA or the compound of formula IB may be deprotected (e.g. by treatment in the presence of acid, e.g., TFA, as described hereinafter) to form a moiety of formula IC, $H_2N\text{-}A^1\text{-CONH}-$  IC or a compound of formula ID, $H_2N\text{-}A^1\text{-CONH}-B^1$  ID wherein, in both cases, $PG^1$ and $A^1$ and, in the case of the compound of formula ID, $B^1$ are as hereinbefore defined.

The moiety of formula IC and/or the compound of formula ID may thereafter be employed as the amine in the process of the invention, thereby forming a polyamide. Hence, in another embodiment of the invention, there is provided a process for the preparation of a polyamide, characterised in that the process comprises a process of the invention as hereinbefore described.

For example, a moiety of formula IC or a compound of formula ID may be employed in the process of the invention, i.e. as the amine, and be reacted in the presence of a compound of formula I, thereby forming a moiety of formula IE, $PG^1\text{-HN-}A^1\text{COHN-}A^1\text{-CONH}-$  IE or a compound of formula IF, $PG^1\text{-HN-}A^1\text{COHN-}A^1\text{-CONH}-B^1$  IF wherein, in each case, $PG^1$ and $B^1$ are as hereinbefore defined, and each $A^1$ independently represents $A^1$ as hereinbefore defined (i.e. each $A^1$ group may be the same or different).

Thereafter, the protecting group $PG^1$ of the moiety of formula IE, or the compound of formula IF may be removed, thereby forming "free" amines, which may be employed in the process of the invention to form a further amide linkage. In this manner a polyamide structure may be built up, i.e. the following polyamide of formula IG may be formed, $X^1-(-HN\text{-}A^1\text{-CO}-)_n NH-B^1$  IG wherein $X^1$ represents $-PG^1$, $-H$ (if any protecting group has been removed), $-C(O)A^1$ (i.e. by a final reaction with a carboxylic acid of formula IH, $A^1\text{-C(O)OH}$, in which $A^1$ is as hereinbefore described, but in which it does not contain an amino group) or another terminal substituent as defined below, n represents an integer of one (when the compound of formula IG is an amide monomer) or more (so forming a polyamide; when n represents 2 or more) and $B^1$ and each $A^1$ (which may be the same or different) are as hereinbefore defined, which is also referred to below as "a process of the invention". Other possible terminal substituents include:

1. Positively charged amines (for increased DNA binding affinity in the case of the DNA-binding polyamides),
2. Conjugating groups (e.g. terminal and internal alkynes, azides, dienes, tertiary phosphines, biotin, fluorescent tags, carboxyl groups, amines),
3. Other DNA-interacting molecules (such as intercalators, PNA, minor groove binders, DNA-binding peptides, cell penetrating peptides, polyamines, oligonucleotides), and
4. Linkers (e.g. PEG) for the attachment of fluorophores, nanoparticles etc.

Such a process for preparing a polyamide is characterised in that at least one (preferably the majority, e.g. all) of the amide coupling steps comprises an amide coupling process of the invention as hereinbefore described (i.e. reaction of an amine with a compound of formula I in the presence of triphosgene). The term "amino acid monomer" when used herein may refer to an amino acid monomer unit, i.e. a moiety "—HN-A-CO—".

Deprotection steps mentioned herein may be performed under standard conditions known in the art. For example, in the case of deprotection of a $PG^1$ moiety, the deprotection may be in the presence of an acid, such as a mild acid (e.g. a weak organic acid, such as TFA). In the case of Fmoc groups, deprotection may be performed in the presence of a base.

In an embodiment of the invention, a polyamide that may be produced is one that contains at least four (—HN-$A^1$-CO—) monomer units (i.e. n is four or more), e.g. at least six e.g. at least eight (such as nine). In a further embodiment, the polyamide that is produced is a hairpin polyamide. In yet a further embodiment, the polyamide that is produced is a cyclic polyamide. In another embodiment, the polyamide that is produced is a straight-chain polyamide (ie not a cyclic polyamide or a cyclic polyamide).

By "hairpin polyamide", we mean that the polyamide has a substantially U-shaped (or "bent") structure. That is, it consists of two polyamide strands that are antiparallel, which arrangement may be achieved by synthesising a first "linear" polyamide strand consisting of aromatic amino acids monomers, attaching it to an aliphatic amino acid monomer, which in turn is attached to a second linear polyamide strand consisting of aromatic amino acids monomers (in which the polyamide is synthesised in accordance with the process(es) of the invention described herein). In this instance, the aliphatic amino acid monomer (linking the linear aromatic acid monomer strands) provides a turning point for to create the antiparallel arrangement. This turn may be termed a γ-turn. Such a hairpin polyamide may achieve a particular binding affinity to DNA. However, the skilled person will appreciate that alternative shapes of the polyamide may be desired depending on the binding abilities required, and alternatives polyamides may be achieved using the process(es) of the invention described herein. Other possible polyamides included H-pin, u-pin and twisted polyamides.

By "cyclic polyamide", we mean a polyamide in which the terminal amino acid monomer forms a further direct linkage to the first amino acid monomer, thereby forming the following cyclic polyamide of formula III,

III in which n is as hereinbefore defined, and each $A^1$ is independently as hereinbefore defined, and a cycle is formed by the linkage of the amino group of a terminal amino acid monomer with the —C(O)— moiety of the first amino acid monomer of the polyamide.

The formation of a cyclic polyamide may be achieved by providing a further linkage for a hairpin polyamide between the first and terminal amino acid monomer. Typically, the further linkage consists of an aliphatic amino acid, which (in the case of the linkage of a hairpin polyamide) may create a second γ-turn, thereby producing a cyclic structure.

In a further embodiment of the invention, the formation of a cyclic polyamide may be achieved by starting the process of the invention with an amine, in which the —$NH_2$ group is attached to a nitrogen heteroatom (e.g. so forming a —N(H)—$NH_2$ moiety), for example a compound of formula IV,

$E^1$-N(H)—$NH_2$     IV wherein $E^1$ represents an optionally substituted aliphatic or aromatic group. Hence, the following compound of formula V may be produced by the process(es) of the invention described herein:

$PG^1$-(—HN-$A^1$-CO—)$_n$N(H)—N(H)-$E^1$     V wherein $PG^1$, n, $E^1$ and each $A^1$ are as hereinbefore defined, which compound may be deprotected (to remove $PG^1$), and then oxidised to form the corresponding compound of formula VI, H—(—HN-$A^1$-CO—)$_n$N=N-$E^1$     VI wherein $PG^1$, n, $E^1$ and each $A^1$ are as hereinbefore defined, wherein the oxidation conditions are suitable to effect the conversion of the —N(H)—N(H)— moiety to the —N=N— moiety, for example, it may be effected by mild oxidation conditions, e.g. treating the deprotected compound of formula V with a solution N-bromosuccinimide and pyridine (e.g. in a solution of DCM).

Thereafter, the compound of formula VI may undergo an intramolecular cyclisation to form a compound of formula III as hereinbefore defined for example, which cyclisation may be promoted by, as a first step, reaction in the presence of a suitable base (e.g. an organic amine base, such as triethylamine), optionally in the presence of a suitable solvent (e.g. a polar aprotic solvent, such as dimethylformamide), which may mixture may be allowed to react for an appropriate period of time (e.g. 24 hours or more, e.g. about 72 hours), followed by hydrogenation (e.g. in the presence of a precious metal catalyst, e.g. palladium, e.g. Pd/C, and $H_2$; which reaction may be allowed to react for an appropriate period of time (e.g. about 2 hours).

Figure 4:
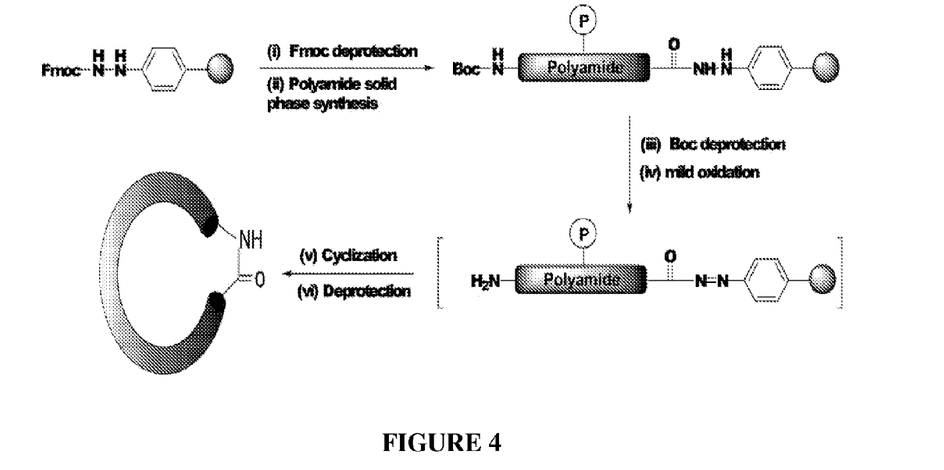
FIG. 4 is an example of a cyclic polyamide synthetic procedure.

The procedure, involving polyamide scaffold construction, intramolecular cyclisation and concomitant resin cleavage all occurring on the solid support (which may provide a more facile route to cyclic polyamides) is depicted in FIG. 4.

In a further embodiment of the invention, the coupling reaction (e.g. polyamide synthesis) may be automated.

In a further embodiment of the invention, there is provided a cyclic polyamide characterised in that there are at least two (e.g. two) groups present, which are capable of carrying a positive charge (e.g. a —$NH_2$, which may be positively charged to form a —$NH_3^+$ group). Preferably, these groups are located on different amino acid monomers (e.g. aliphatic amino acid monomers), and, in particular, they are located at the (aliphatic amino acid monomers on the) γ-turns. Advantageously, such polyamides carrying more than one charge may display improved binding affinities to e.g. DNA sequences.

As stated above, the cyclic polyamide of formula III may be prepared by linking a hairpin polyamide. Such a hairpin polyamide may contain, at the γ-turn, one or more (e.g. one) substituent(s) that is/are capable of carrying a positive charge (e.g. a —$NH_2$, which may be positively charged to form a —$NH_3^+$ group). Advantageously, a cyclic polyamide prepared in accordance with the procedure described above from a hairpin polyamide may also contain, at the second γ-turn, one or more (e.g. one) substituent(s) that is/are capable of carrying a positive charge (e.g. when the final linkage consists of an aliphatic amino acid linkage between the first and terminal amino acid monomer units of a hairpin polyamide). Hence, in such an embodiment, there is provided a group capable of carrying a positive charge on each of the two γ-turns (which consist of an aliphatic amino acid monomer). Advantageously, this is achieved by the novel method of forming a cyclic polyamide by the intramolecular cyclisation reaction described herein. Further charges may be incorporated via appropriately substituted Pyrrole and Imidazole building blocks. By replacing the N-methyl group of the Py and Im with an alkyl azide or another protected amine function, multiple positive charges may be incorporated.

In a further embodiment of the invention, the amine employed in the process of the invention (e.g. of formula II, $H_2N$—$B^1$) is bound to a resin (any suitable resin, such as a polyacrylamide (PAM) resin), and hence the synthesis of the amide (or polyamide) is a solid phase synthesis, which may allow for a facile synthesis of a polyamide by the stepwise building of the individual elements. This amine is preferably bound to the resin by the $B^1$ moiety.

In another embodiment of the invention, the synthesis of polyamides or their trimeric, dimeric or tetrameric building blocks can be prepared using solution phase synthetic Methodologies. Thus, it will be appreciated that the synthesis is modular for the preparation of shorter polyamide sequences which would increase the flexibility of the approach for potential scale-up.

In a further embodiment of the invention, when $B^1$—$NH_2$ represents —C(O)—($C_{1-6}$ alkyl)-$NH_2$ (thereby forming a moiety of formula —C(O)—($C_{1-6}$ alkyl)-NH—; which is attached to the resin via the first hyphen), then the attachment to the resin may be cleaved by reaction in the presence of an amine (e.g. one of formula VII as defined below), which may either form a further amide linkage with the —C(O)— moiety, or, may replace the $B^1$—NH— moiety of the amide/polyamide (for instance, when $B^1$—NH— is a hydrazide, e.g. $E^1$-NH—NH—). For instance, such an amine may be of formula VII, $$Q^1\text{-}NH_2 \qquad \text{VII}$$

wherein $Q^1$ represents optionally substituted aliphatic moiety, preferably such as one defined herein in respect of $A^1$, thereby forming the following compounds (or deprotected derivatives thereof) pursuant to the processes described herein:

(i) from a compound of formula IB in which $B^1$ represents —C(O)—($C_{1-6}$ alkyl)- (the first hyphen representing the point of attachment to the resin), a compound of formula VIIB (i), $$PG^1\text{-}HN\text{-}A^1\text{-}CONH\text{-}Q^1 \qquad \text{VIIB(i)}$$

or, a compound of formula VIIB(ii)

$$PG^1\text{-}HN\text{-}A^1\text{-}CONH\text{—}(C_{1-6}\text{ alkyl})\text{-}C(O)NH\text{-}Q^1 \qquad \text{VIIB (i)}$$

(ii) from a compound of formula IF in which $B^1$ represents —C(O)—($C_{1-6}$ alkyl)- (the first hyphen representing the point of attachment to the resin), a compound of formula VIIF(i)

$$PG^1\text{-}HN\text{-}A^1COHN\text{-}A^1\text{-}CONH\text{-}Q^1 \qquad \text{VIIF(i)}$$

or, a compound of formula VIIF(ii), $$PG^1\text{-}HN\text{-}A^1COHN\text{-}A^1\text{-}CONH\text{—}(C_{1-6}\text{ alkyl})\text{-}C(O)NH\text{-}Q^1 \qquad \text{VIIF(ii)}$$

(iii) from a compound of formula IG in which $B^1$ represents —C(O)—($C_{1-6}$ alkyl)- (the first hyphen representing the point of attachment to the resin), a compound of formula VIIG(i)

$$X^1\text{—}(\text{—}HN\text{-}A^1\text{-}CO\text{—})_n NH\text{-}Q^1 \qquad \text{VIIG(i)}$$

or, a compound of formula VIIG(ii), $$X^1\text{—}(\text{—}HN\text{-}A^1\text{-}CO\text{—})_n NH\text{—}(C_{1-6}\text{ alkyl})\text{-}C(O)NH\text{-}Q^1 \qquad \text{VIIG(ii)}$$

wherein, in all cases, each $X^1$, $A^1$, $Q^1$, n, and $PG^1$ are as defined herein.

The present application is also applicable to the use of sulphonamide safety catch resin linkers. In this situation, the terminal carboxyl group of the polyamide is connected to the resin or solid support by a sulphonamide linkage, ie —NH—$SO_2$—(RESIN).

The above also applies to the amine of formula IV, which may also be bound to a resin in a similar manner, for example via the $E^1$ moiety. In this instance, in a preferred embodiment of the invention, when the compound of formula V so formed is deprotected and oxidised (to form a compound of formula VI), then the intramolecular cyclisation step to form a cyclic polyamide of formula III has the additional advantage that it may be accompanied by cleavage from the resin support. Hence, the need to separately cleave the polyamide from the resin is circumvented as the intramolecular cyclisation occurs with concomitant cleavage from the resin. Clearly, this is advantageous in terms of efficiency, as an additional synthetic step is circumvented.

Unless otherwise specified, alkyl groups as defined herein may be straight-chain or, when there is a sufficient number (i.e. a minimum of three) of carbon atoms be branched-chain, and/or cyclic. Further, when there is a sufficient number (i.e. a minimum of four) of carbon atoms, such alkyl groups may also be part cyclic/acyclic. Such alkyl groups may also be saturated or, when there is a sufficient number (i.e. a minimum of two) of carbon atoms, be unsaturated.

The term "aryl", when used herein, includes $C_{6-10}$ groups. Such groups may be monocyclic, bicyclic or tricyclic and, when polycyclic, be either wholly or partly aromatic. $C_{6-10}$ aryl groups that may be mentioned include phenyl, naphthyl, and the like. For the avoidance of doubt, the point of attachment of substituents on aryl groups may be via any carbon atom of the ring system.

The term "heteroaryl", when used herein, includes 5- to 14-membered heteroaryl groups containing one or more heteroatoms selected from oxygen, nitrogen and/or sulfur. Such heteroaryl group may comprise one, two or three rings, of which at least one is aromatic. Substituents on heteroaryl groups may, where appropriate, be located on any atom in the ring system including a heteroatom. The point of attachment of heteroaryl groups may be via any atom in the ring system including (where appropriate) a heteroatom. Examples of heteroaryl groups that may be mentioned include pyridyl, pyrrolyl, quinolinyl, furanyl, thienyl, oxadiazolyl, thiadiazolyl, thiazolyl, oxazolyl, pyrazolyl, triazolyl, tetrazolyl, isoxazolyl, isothiazolyl, imidazolyl, pyrimidinyl, indolyl, pyrazinyl, indazolyl, pyrimidinyl, quinolinyl, benzoimidazolyl and benzthiazolyl.

The term "halo", when used herein, includes fluoro, chloro, bromo and iodo.

In the process of the invention at least one equivalent (compared to the amine) of the amino acid should be employed in the process of the invention, for example for each step in the build-up of a polyamide. However, it is preferred the amino acid is employed in excess, e.g. at least two equivalents, e.g. more than three such as about four equivalents.

The coupling reaction of the process of the invention may be performed in the presence of any suitable solvent. However, it is preferred that the reagents (amine and amino acid) are dissolved into a polar aprotic solvent (preferably THF; preferably anhydrous). When a solid phase synthesis is performed, the actual quantity of solvent may be minimal (e.g. when between about 0.01 and about 0.1 moles are the reagents are employed, it may be about 1 mL). Base may also be employed in the process of the invention, for instance collidine (which may be employed in excess, e.g. more than 1 equivalent, e.g. more than 5 equivalents, e.g. about 12 equivalents). The base may be added to the reaction mixture (plus solvent, if present).

The process of the invention is not limited to any particular amino acid (i.e. the compound of formula I may be any suitable protected amino acid), and includes aliphatic and aromatic amino acids. The diversity of amino acids is applicable in this case, given that it has been surprisingly found that the process of the invention is compatible with an acid-sensitive protecting group $PG^1$ (e.g. t-Boc) attached to an amino acid.

However, certain amino acids are preferred. For example, each $A^1$ (at each occurrence when used herein) preferably represents:

an aryl group optionally substituted by one or more substituents selected from $J^1$;
a heteroaryl group optionally substituted by one or more substituents selected from $J^2$;
$C_{1-12}$ alkyl in which alkyl group a carbon atom is optionally replaced by a heteroatom (e.g. —N(H)—, —O— or —S—), and which alkyl group is optionally substituted by one or more substituents selected from $J^3$;
each $J^1$, $J^2$ and $J^3$ independently represents, at each occasion when used herein, halo, —$NO_2$, —CN, —$C(O)_2R^{x1}$, —$OR^{x2}$, —$SR^{x3}$, —$S(O)R^{x4}$, —$S(O)_2R^{x5}$, —$N(R^{x6})R^{x7}$, —$N(R^{x8}, C(O)R^{x9}$, —$N(R^{x10}S(O)_2R^{x11}$ or $R^{x12}$;
$R^{x1}$, $R^{x2}$, $R^{x3}$, $R^{x6}$, $R^{x7}$, $R^{x8}$, $R^{x9}$ and $R^{x10}$ independently represent hydrogen or $C_{1-6}$ alkyl optionally substituted by one or more halo (e.g. fluoro) atoms;
$R^{x4}$, $R^{x5}$, $R^{x11}$ and $R^{x12}$ independently represent $C_{1-6}$ alkyl optionally substituted by one or more halo (e.g. fluoro) atoms;
substituents, e.g. —$NH_2$ substituents, may also be protected by protecting groups (such as those defined hereinafter).

Preferred compounds that may be prepared by the process(es) of the invention described herein include:
when $A^1$ represents optionally substituted aryl, then it preferably represents optionally substituted phenyl;
when $A^1$ represents optionally substituted heteroaryl, then that heteroaryl group is preferably a 8- to 10-membered bicyclic heteroaryl group or a 5- or 6-membered monocyclic heteroaryl group;
when $A^1$ represents a 5- or 6-membered monocyclic heteroaryl group, then that group may contain one to four heteroatoms (preferably one or two heteroatoms selected from nitrogen, oxygen and sulfur);
when $A^1$ represents a 8-, 9- or 10-membered bicyclic heteroaryl group, then that group preferably consists of a 5- or 6-membered ring fused to another 5- or 6-membered ring (in which either one of those rings may contain one or more (e.g. four, or, preferably one to three) heteroatoms), in which the total number of heteroatoms is preferably one to four (in an embodiment, such a bicyclic group is 9- or 10-membered and consists of a phenyl ring fused to a 5- or 6-membered monocyclic heteroaryl group as hereinbefore defined;
when $A^1$ represents an optionally substituted aliphatic group, then it preferably represents $C_{1-6}$ alkyl (e.g. $C_{1-3}$ alkyl);
$J^1$, $J^2$ and $J^3$ substituents are preferably selected from halo, —$N(R^{x6})R^{x7}$ and $R^{x12}$ (e.g. $C_{1-6}$ alkyl, such as methyl);
$R^{x6}$ and $R^{x7}$ independently represent hydrogen (so forming a —$NH_2$ group, which may be protected as defined herein, or may exist as —$NH_{3+}$).

In the processes described herein, preferably:
$B^1$ is attached to a resin (and the synthesis is therefore a solid phase synthesis);
$B^1$ may represent —C(O)—($C_{1-6}$ alkyl)-$NH_2$ (wherein the first hyphen represents the point of attachment to the resin), for example, —C(O)—$CH_2$—$CH_2$—$NH_2$;
$B^1$ may also represent -(optionally substituted aryl)-N(H)—$NH_2$ (in which the first hyphen represents the point of attachment to the resin), for example, phenyl substituted in the 4-position with a —N(H)—$NH_2$ group (i.e. $E^1$ represents phenyl).

1 $R_1 = CH$, $R_2 = N$, $R_3 = N$, $R_4 = \beta$-Ala-Dp
2 $R_1 = N$, $R_2 = N$, $R_3 = CH$, $R_4 = \beta$-Ala-Dp

β-Ala =

Dp =

Most preferred compounds that may be prepared by the process(es) of the invention include those in which:
hairpin polyamides are prepared by linking together, with an aliphatic amino acid monomer (as defined herein), two strands of monomer units consisting of aromatic or heteroaromatic amino acid monomers;
each strand of aromatic or heteroaromatic amino acid monomers in the hairpin (or cyclic) polyamide comprises one or more monomer units (preferably each strand consists of the same number of monomer units, e.g. two, three or preferably four);
in the case of a hairpin polyamide, n preferably represents three or more (e.g. five or more, and preferably, seven or more, e.g. nine; in the case of the latter, this would consist of four amino acid monomers in each strand plus one aliphatic amino acid monomer linking the respective strands);
cyclic polyamides are prepared by linking together (e.g. the first and terminal amino acid monomer) a hairpin polyamide (such as one described herein) with an aliphatic amino acid monomer (for example, in accordance with the procedures described herein);
in the case of a hairpin polyamide, n preferably represents four or more (e.g. six or more, and preferably, eight or more, e.g. ten; in the case of the latter, this would consist of four amino acid monomers in each strand plus one aliphatic amino acid monomer linking each of the respective ends of the strands).

Most preferred compounds that may be prepared by the process(es) of the invention include those in which in a hairpin or cyclic polyamide (prepared from a hairpin polyamide):
the amino acids of the γ-turns, are aliphatic amino acid monomers, preferably, in which $A^1$ represents $C_{1-3}$ alkyl (e.g. n-propyl), preferably substituted with one or more (e.g. one to three; preferably one) substituent(s) selected from $J^3$;
$Q^1$ may represent $C_{1-6}$ (e.g. $C_{1-3}$) alkyl optionally substituted by one or more substituents selected from $J^3$ (so forming, e.g. a $-CH_2CH_2CH_2-N(CH_3)_2$ group);

$J^3$ represents $-N(R^{x6})R^{x7}$;
$R^{x6}$ and $R^{x7}$ independently represent $C_{1-2}$ alkyl (e.g. methyl) or hydrogen; the amino acids of the strands are preferably heteroaromatic amino acid monomers, in particular those in which each $A^1$ independently represents a 5-membered monocyclic heteroaryl group (preferably containing one or two heteroatoms, preferably a nitrogen heteroatom(s)), for example, pyrrolyl or imidazolyl (e.g. in which the $-C(O)-$ moiety is preferably attached to the 2-position and the $-N(H)-$ moiety is attached to the 4-position), which heteroaryl groups are optionally substituted by one or more (e.g. one) substituent(s) selected from $J^2$ (when the substituent is $R^{x12}$, then it is preferably located on the 1(N)-nitrogen of such pyrrolyl or imidazolyl groups);
$J^2$ represents $R^{x12}$;
$R^{x12}$ represents $C_{1-6}$ (e.g. $C_{1-3}$) alkyl, (such as methyl).
Preferred aliphatic amino acid monomer units that may be mentioned include $-HN-CH_2-CH_2-C(-NH_2)(H)-C(O)-$, or amino protected derivatives thereof. That is $A^1$ in these instances represents $-CH_2-CH_2-C(-NH_2)(H)-$.
Preferred aromatic amino acid monomer units that may be mentioned include:

i.e. in these instances, $A^1$ represents 1-methyl-pyrrolyl or 1-methyl-imidazolyl, each of which are linked to the $-NH-$ moiety at the 4-position and to the —C(O)— moiety at the 2-position. Other possible monomer units include analogs of these compounds with substituents on the 1-methyl group. Benzimidazoles and indazole derivatives are also preferred aromatic amino acid monomer units.

Particularly preferred amino acid monomer units (and polyamides, including hairpin and cyclic polyamides) are those of the examples described hereinafter.

It is stated above that $R^1$ represents a secondary or tertiary $C_{3-8}$ alkyl group. By this, we mean that the alkyl group is secondary or tertiary with respect to the point of attachment to the oxygen atom of the requisite carbamate moiety, i.e. a to the —OC(O)N(H)— moiety of the protecting group $PG^1$. Preferably, $R^1$ represents a tertiary $C_{4-8}$ (e.g. $C_{4-6}$) alkyl group, and most preferably $R^1$ represents tert-butyl (so forming a t-Boc protecting group).

The skilled person will appreciate that when $R^1$ is a secondary or, preferably, a tertiary alkyl group, then the protecting group may be labile to acid, due to the formation of a relatively stable carbocation in the mechanism of the deprotection step (accompanied by the release of carbon dioxide). Tertiary carbocations are the most stable and hence why protecting groups in which $R^1$ represents a tertiary alkyl group are the most preferred. In contrast, if $R^1$ represented a primary alkyl group (i.e. forming a protecting group in which there is no branching of the alkyl group at the position α to the —OC(O)N(H)— moiety, but, rather, e.g. a —$CH_2$— moiety), then such protecting groups are typically not labile to acid. This is due to the fact that the mechanism of acid promoted deprotection would proceed via a primary carbocation, which is not stable and hence why such protecting groups would not be labile to acid. A example of such a protecting group is a fluorenylmethyloxycarbonyl (Fmoc) protecting group, which consists of a carbamate as defined by $PG^1$ (i.e. —C(O)$OR^1$), but in which the $R^1$ group represents a primary alkyl group, i.e. there is no branching at the position α to the point of attachment of the $R^1$ group to the —OC(O)—N(H)— moiety. Such a Fmoc protecting group is not labile to acid, but in stark contrast, is labile to base, due to the acidic proton in the position β to the —OC(O)—N(H)— moiety.

The skilled person will appreciate that due to the fact that different protecting groups (e.g. an acid-sensitive one and a base-sensitive one) have fundamentally different chemical reactivities, in peptide coupling reaction it cannot necessarily be considered to be the case that a coupling reagent employed for e.g. a Fmoc-protected amino acid will work in the same way as e.g. a Boc-protected amino acid. For example, it might be expected that triphosgene employed in the process of the invention may produce an acid chloride (e.g. phosgene) in situ, which may be acidic enough to cleave the acid-labile protecting group defined by $PG^1$ (e.g. t-Boc). However, unexpectedly, it has been found that triphosgene is compatible with the relevant $PG^1$ groups that protect the amino acids employed in the process of the invention, i.e. that the triphosgene does not cause substantial cleavage of the acid-labile protecting group $PG^1$ (e.g. t-Boc).

Advantageously, the process of the invention proceeds despite the presence of a protecting group $PG^1$ (e.g. t-Boc) that is labile to acid. Hence, the reaction unexpectedly proceeds with a greater efficiency (thereby producing a better yield) and/or with less undesired side-products (resultant of undesired reactions, such as deprotection of the Boc group, and competing coupling reactions).

It is stated herein that specific functional groups may be protected. It will also be appreciated by those skilled in the art that, in the processes described above, other functional groups of intermediate compounds may be, or may need to be, protected by protecting groups. Specific amino protecting groups that may be mentioned include the Boc, Fmoc and Cbz protecting groups.

The protection and deprotection of functional groups may take place before or after any of the reaction steps described hereinbefore. Protecting groups may be removed in accordance with techniques which are well known to those skilled in the art and as described hereinafter. The use of protecting groups is described in "Protective Groups in Organic Chemistry", edited by J. W. F. McOmie, Plenum Press (1973), and "Protective Groups in Organic Synthesis", 3$^{rd}$ edition, T. W. Greene & P. G. M. Wutz, Wiley-Interscience (1999).

The process of the invention may have the advantage that, for example when a solid or solution phase synthesis method is effected in the manner indicated above, automation of the process may be facilitated (compared with current processes, e.g. which may use triphosgene as the activating agent in a coupling reaction, but in the presence of an alternative protecting group to that employed in this process, such as a Fmoc group).

In general, the processes described herein, may have the advantage that compounds of formula may be produced in a manner that utilises fewer reagents and/or solvents, and/or requires fewer reaction steps (e.g. distinct/separate reaction steps) compared to processes disclosed in the prior art.

The processes of the invention may also have the advantage that compounds are produced in higher yield, in higher purity, in higher selectivity (e.g. higher regioselectivity), in less time, in a more convenient (i.e. easy to handle) form, from more convenient (i.e. easy to handle) precursors, at a lower cost and/or with less usage and/or wastage of materials (including reagents and solvents) compared to the procedures disclosed in the prior art.

The following examples are merely illustrative examples of the processes of the invention described herein.

EXPERIMENTAL PROCEDURES

Abbreviations

BTC, Bis-(trichloromethyl)-carbonate; DCC, N,N'-Dicyclohexyl carbodiimide; DCM, dichloromethane; DIEA, N-ethyldiisopropylamine; DMF, N,N'-dimethylformamide; DMPA, 3-Dimethylaminopropylamine; Fmoc-D-Dab(Boc)-OH, N-α-(9-fluorenylmethyloxy-carbonyl)-N-γ-tbutyloxycarbonyl-D-2,4-diaminobutyric acid; NBS, N-bromosuccinimide; TEA, triethylamine; TFA, Trifluoroacetic acid; Z-D-Dab(Boc)-OH, Z—N-γ-Boc-D-2,4-diaminobutyric acid.

Experimental Section:

General. All reagents were HPLC or peptide synthesis grade. DMF, DCM, TFA, and DCC were obtained from Acros Organics. BTC, DIEA and DMPA were purchased from Sigma-Aldrich. 4-Fmoc-hydrazinobenzoyl AM NovaGel resin was purchased from Novabiochem. Fmoc-D-Dab(Boc)-OH was purchased from ABCR. Z-D-Dab(Boc)-OH was purchased from CHEM-IMPEX International. Boc-β-Ala-Pam Resin was purchased from Peptides International.

Boc-Py-OH, Boc-Im-OH and N-methylimidazole carboxylic acid were prepared according to the literature.

Analytical and semipreparative RP-HPLC was performed at room temperature on the ULTIMAT 3000 Instrument (DIONEX). UV absorbance was measured using a photodiode array detector at 260 and 310 nm. An ACE C18 column (4.6×250 mm, 5 µm, 300 Å) was used for analytical RP-HPLC. For semi-preparative HPLC, an ACE C18 column

Example A

Synthesis of Polyamide Sequence 1 (Solid Phase)

Figure 1:
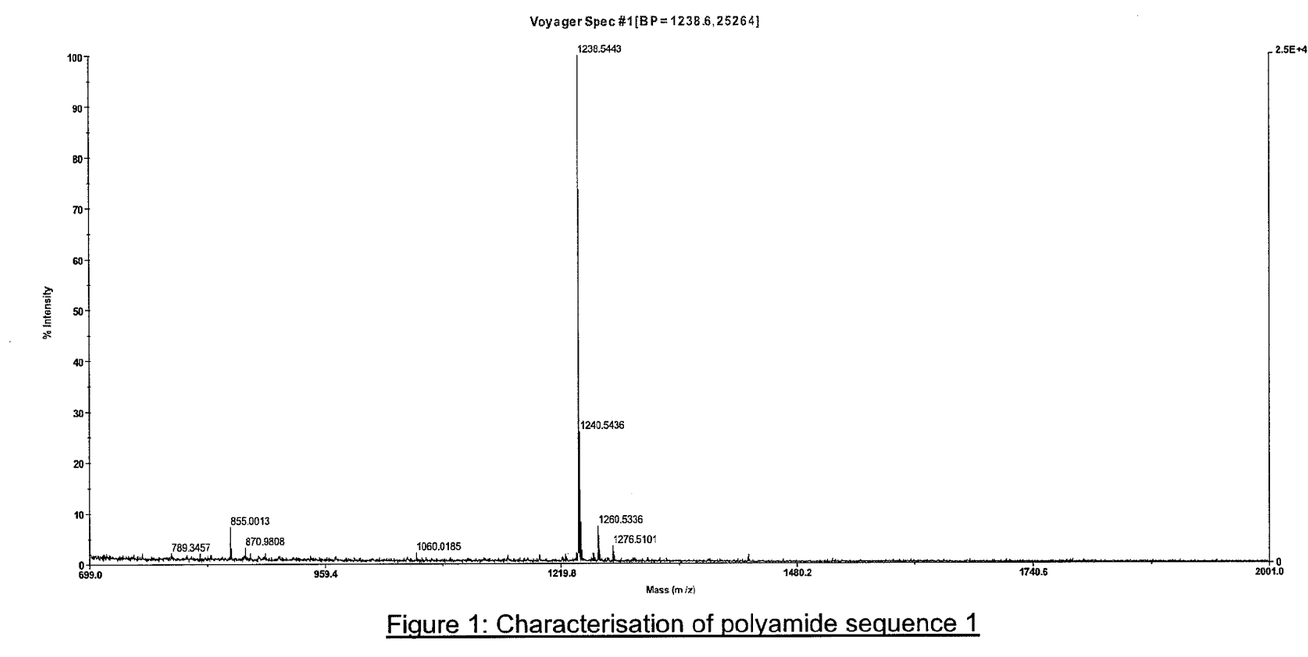
FIG. 1 is a mass spectrum of the polyamide of sequence 1 as produced in Example A.
Figure 5:
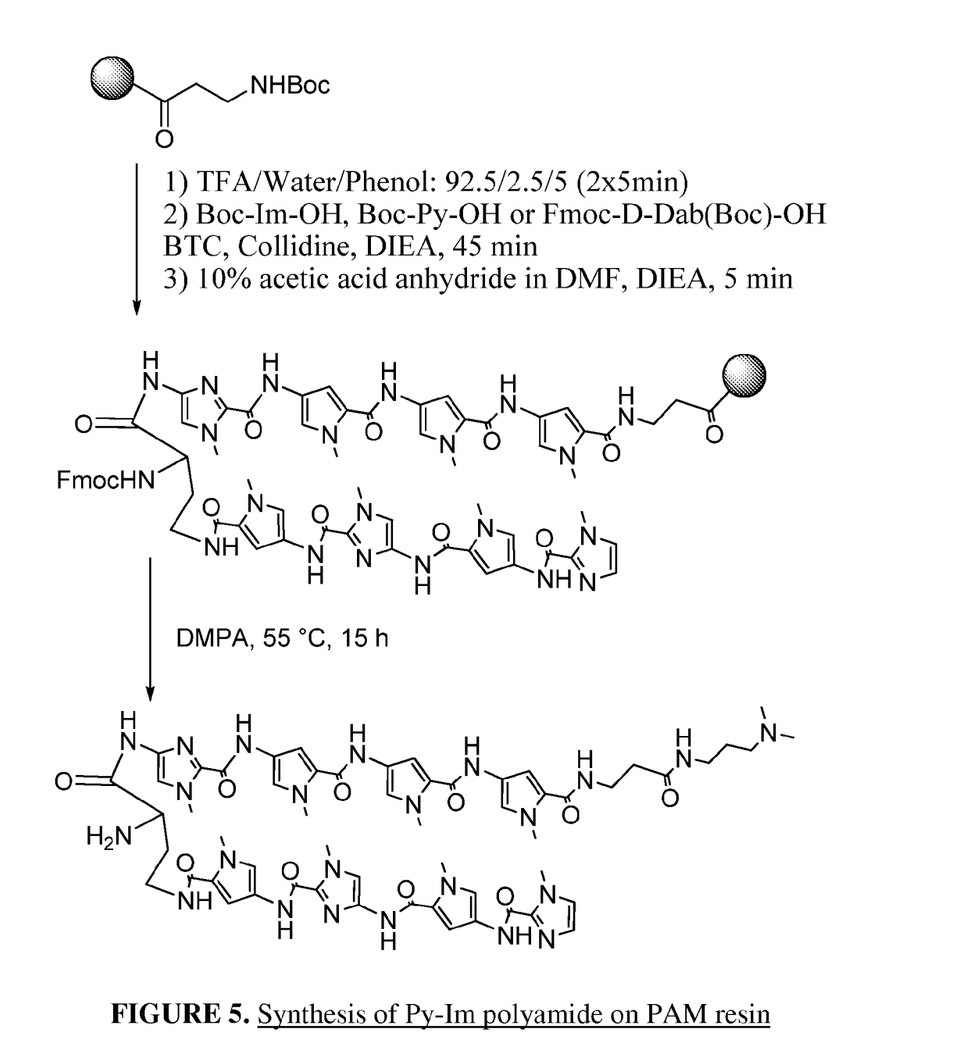
FIG. 5 is an example of the synthesis of Py-Im polyamide on PAM resin.

Polyamide synthesis was performed manually in a 10 mL peptide synthesis vessel by solid-phase Boc-chemistry (Scheme-1). Boc-β-Ala-PAM resin was used as a solid support at a substitution level of 0.26 mmol/g (100 mg, 0.026 mmol). The Boc (i.e. t-Boc) protecting group was removed by TFA deprotection using appropriate reagents (TFA/Water/Phenol: 92.5/2.5/5). After washing, the resin was treated with 1 mL dry THF for 10 min. Meanwhile, the following Boc-protected amino acid (4 eq) and BTC (1.3 eq) were dissolved in 1 mL dry THF. Collidine (12 eq) was added drop by drop to the THF solution. After activating for 1 min, the suspension was added to the deprotected PAM resin following with addition of DIEA (8 eq). The mixture was shaking for 45 min. The resin was drained and rinsed with DMF (4×2 mL). This procedure was repeated until a polyamide sequence (Im-Py-Im-Py-γ(Fmoc)-Im-Py-Py-Py-β) bound to PAM resin was obtained. After washing with DMF (4×2 mL) and MeOH (4×2 mL), the resin was dried under N2. The polyamide sequence was cleaved off the PAM resin with 1 mL DMPA for 15 h at 55° C. The DMPA/PAM resin/polyamide mixture was filtered to remove resin. The filtrate was precipitated by adding 8 volumes of diethyl ether and cooling to −20° C. The crude product was collected by centrifugation and dried under vacuum to produce a light-yellow powdery solid. The crude product was dissolved in 2 mL 10% MeCN/H$_2$O/0.1% TFA. After purification by semi-preparative reversed-phase HPLC, the products were lyophilized to give white powders (10.5 mg, yield 33%). The product was characterized by MALDI-MS: calcd: m/z 1238.32. found: m/z 1238.54 (see FIG. 1 and FIG. 5).

According to the above procedure therefore the following hairpin polyamides were prepared (Scheme 1A):

Example B

Synthesis of Polyamide Sequence 3 (Solid Phase)

Figure 2:
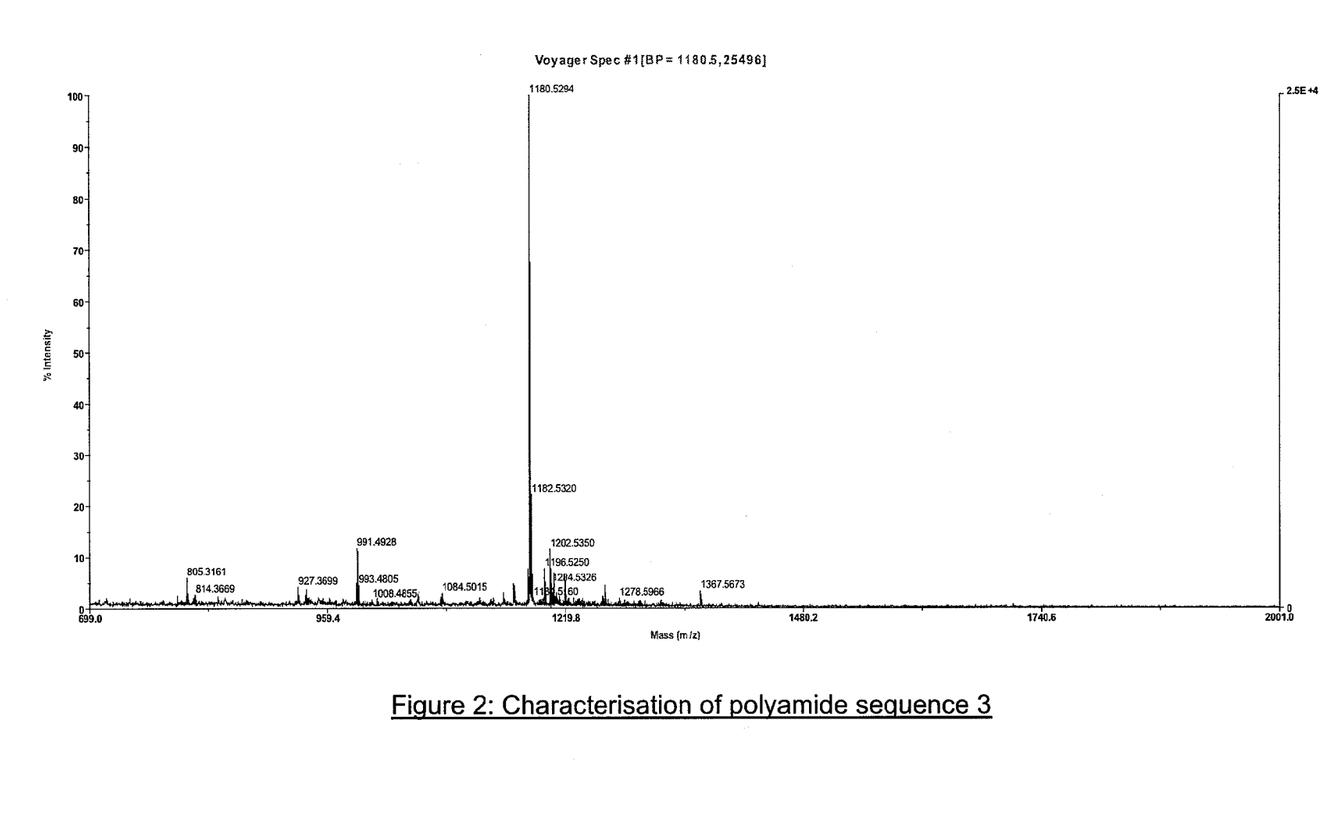
FIG. 2 is a mass spectrum of the polyamide of sequence 3 as produced in Example B.
Figure 6:
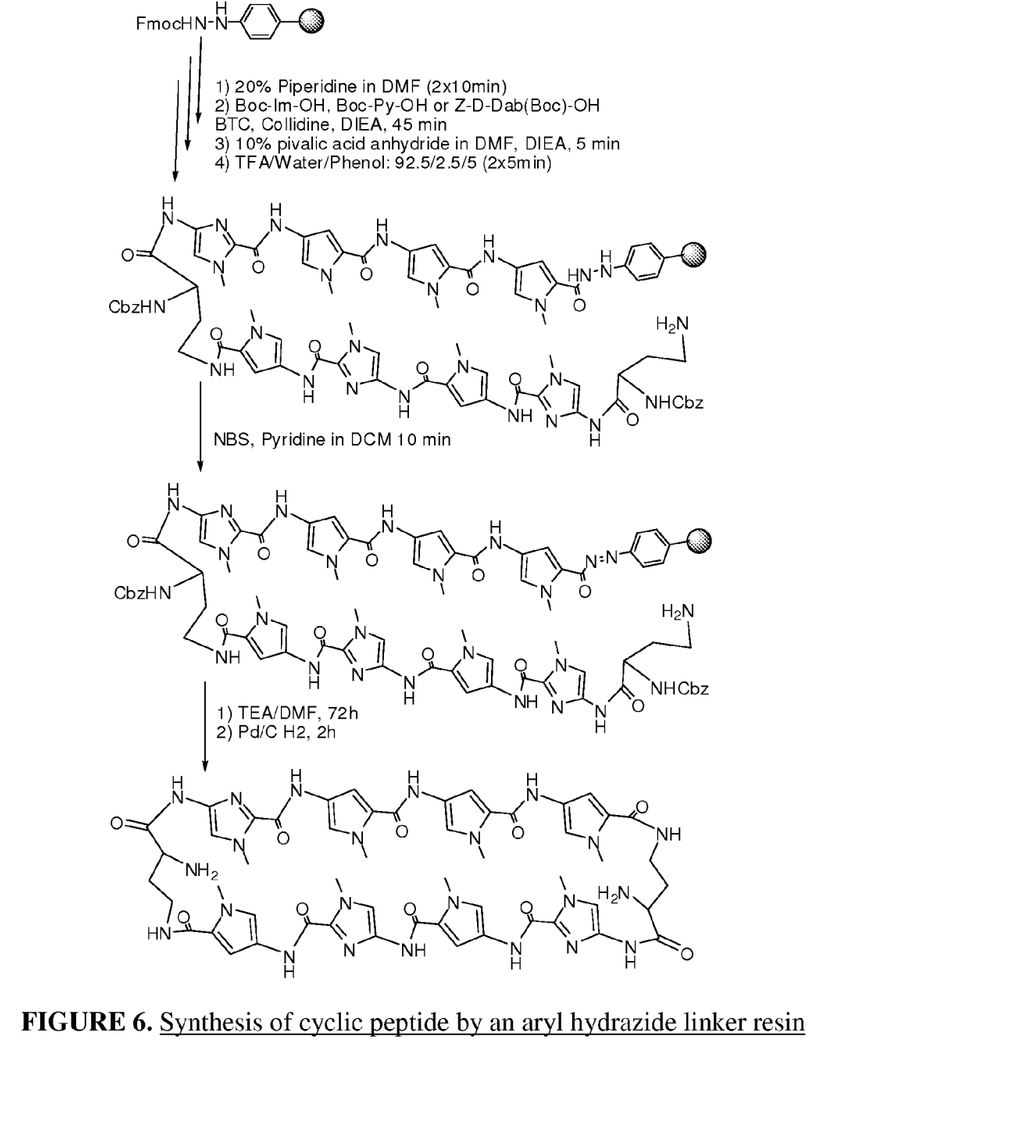
FIG. 6 is an example of the synthesis of a cyclic peptide by an aryl hydrazide linker resin.

Synthesis of cyclised polyamide sequence 3 was performed manually in a 10 mL peptide synthesis vessel by solid-phase Boc-chemistry (Scheme-2). Fmoc-hydrazinobenzoyl AM NovaGel resin (200 mg, 0.030 mmol) was used as a solid support at a substitution level of 0.15 mmol/g. First, the Fmoc group was cleaved with 20% piperidine in DMF. After washing with DMF (4×2 mL), the resin was treated with 1 mL dry THF for 10 min. Meanwhile, the following Boc-protected amino acid (4 eq) and BTC (0.3 eq) were dissolved in 1 mL dry THF. Collidine (12 eq) was added drop by drop to the THF solution. After activating for 1 min, the suspension was added to the deprotected resin followed by addition of DIEA (8 eq). The mixture was shaken for 45 min. After being drained and rinsed with DMF (4×2 mL), the resin was capped with 10% pivalic acid anhydride in DMF for 5 min. The Boc protecting group was then removed by TFA deprotection using appropriate reagents (TFA/Water/Phenol: 92.5/2.5/5). This procedure was repeated until a polyamide sequence (NH$_2$-γ(Z)-Im-Py-Im-Py-γ(Z)-Im-Py-Py-Py) bound to hydrazinobenzoyl resin was obtained. After washing with DMF (4×2 mL), the resin was treated with a solution of NBS and pyridine (2 eq. each) in 3 mL DCM for 10 min, drained and washed with DCM (4×2 mL). The resin was treated with a solution of 5 equiv. of TEA in DCM for 3 days at 40° C. After cooling to room temperature, the resin was drained and washed with DCM (4×2 mL). The filtrates were combined and dried under vacuum. The obtained light-yellow powder was dissolved in 10 mL MeOH. After removing the Cbz protect group with hydrogenation (1 atm, 5% Pd/C, 2 h), the product was purified by semi-preparative reversed-phase HPLC, and lyophilized to give a white powder (2.3 mg, yield 6%). The product was characterized by MALDI-MS: calcd: m/z 1180.20. found: m/z 1180.53 (see FIG. 2 and FIG. 6).

In accordance, with these procedures, the following doubly charged polyamides were prepared (Scheme 2A):

Scheme 1A: where β Ala = β. alanyl; and Dp = dimethyl propylamino.

1 R$_1$ = CH, R$_2$ = N, R$_3$ = N, R$_4$ = β-Ala-Dp   2 R$_1$ = N, R$_2$ = N,  R$_3$ = CH, R$_4$ = β-Ala-Dp

3

The cyclisation and resin cleavage step also proceeded smoothly by final deprotection of the γ-Boc group followed by resin activation and prolonged heating at 40° C. in a NEt$_3$/DMF for 72 hours to afford the desired cyclic polyamide in 90% purity and in 6% overall yield directly after CBz deprotection.

Example C

Comparative Study

Model investigations revealed the efficiency of the coupling reaction between resin bound Im amines and BocPyOH to be only 5-8% when traditional coupling protocols were adopted (Table 1). Although the use of dimers provides a potential alternative to direct coupling of the problematic imidazole amine coupling, their widespread utility in polyamide synthesis to be compromised by their inherent insolubility in typical coupling solvents (e.g. DMF, NMP, DMSO), resulting in the formation of polyamide products in low yield and purity.

The reactivity of the acid chloride generated in situ by the reaction of 0.33 equivalents of BTC with the appropriate carboxylic acid was tested. This considerably enhanced coupling efficiencies. Indeed this BTC method was found to be far superior to current protocols which used DCC/HOAt and HATU [Table 1]. Activation times of both the BocPyOH and BocImOH only required 1 min when BTC was used, compared to 2 hours for DCC/HOAt-mediated activations respectively.[17] Coupling times of 20 min. were required for quantitative coupling using BTC which is comparable to the DCC/HOAt method of Krutzik & Chamberlin and enables each deprotection-coupling-wash cycle to be effected well within one hour.

TABLE 1

Comparative coupling yields of polyamide building blocks.
Yields were based on HPLC peak integration.

| Hetereoaromatic amide bond[a] | HATU (%)[b] | DCC/HOAt (%)[c] | BTC (%)[d] |
|---|---|---|---|
| BocPyOH → H$_2$NIm-Resin | 5 | 8 | >98 |
| BocPyOH → H$_2$NPy-Resin | 95 | 95 | >98 |
| BocImOH → H$_2$NIm-Resin | 12 | >98 | >98 |

[a]Resin = β-Ala PAM;
[b]activation in 1:1 DMF/NMP, Boc-monomer/HATU/DIEA, 3-5 min; coupling for 20 min.
[c]activation in 1:1 DMF/NMP, Boc-monomer/DCC/HOAt, 2 h, DIEA; coupling for 20 min.
[d]activation in THF, Boc-monomer/BTC/Collidine, 1 min, DIEA; coupling for 20 min.

Example D

Comparative Study

We investigated the preparation of challenging hairpin polyamide sequences using the BTC coupling methodology. Polyamide 1 (of Scheme 1A in Example A), which targets the DNA sequence 5'-ATGAGCT-3' with nanomolar affinity, was synthesized in 0.1% yield using the β-Ala PAM resin via a traditional Boc-chemistry/HBTU protocol. The low yield is most likely attributed to a challenging Im-amine BocPyOH coupling late in the synthesis sequence.

Using Boc-chemistry and the BTC protocol, polyamide 1 was prepared in 33% yield after CBz deprotection of the γ-turn motif required for high binding affinity; i.e. this is a 330-fold increase in isolated yield for 1 using our BTC method.

The preparation of polyamides using solid supports that do not install an A,T-encoding β-Ala tail on the C-termini of polyamides was investigated. This is an important requisite for biological applications as A,T encoding tails limit the sequence space in which polyamides could potentially interrogate. As a consequence of their stability in strongly acidic and basic conditions coupled with a mild resin release protocol, aryl hydrazide resins are potentially superior to Kaiser oxime resins currently used for truncated polyamide synthesis.

Example E

Synthesis of Polyamide Sequence 3 (Solution Phase)

Triphosgene (BTC, 0.033 mmol) was added to a solution of BocPyOH (1, 0.1 mmol) and collidine (0.4 mmol) in THF (0.5 mL). The reaction was stirred at room temperature for 1 minute. In a separate vial DIEA (72 uL, 0.4 mmol.) was added to a solution of NH$_2$-Im.HCl-OEt (2, 0.1 mmol) in DMSO: THF (1:1, 0.50 mL) and was quickly added to the solution containing the activated BocPyOH and stirred at RT for 30 min.

Figure 3:
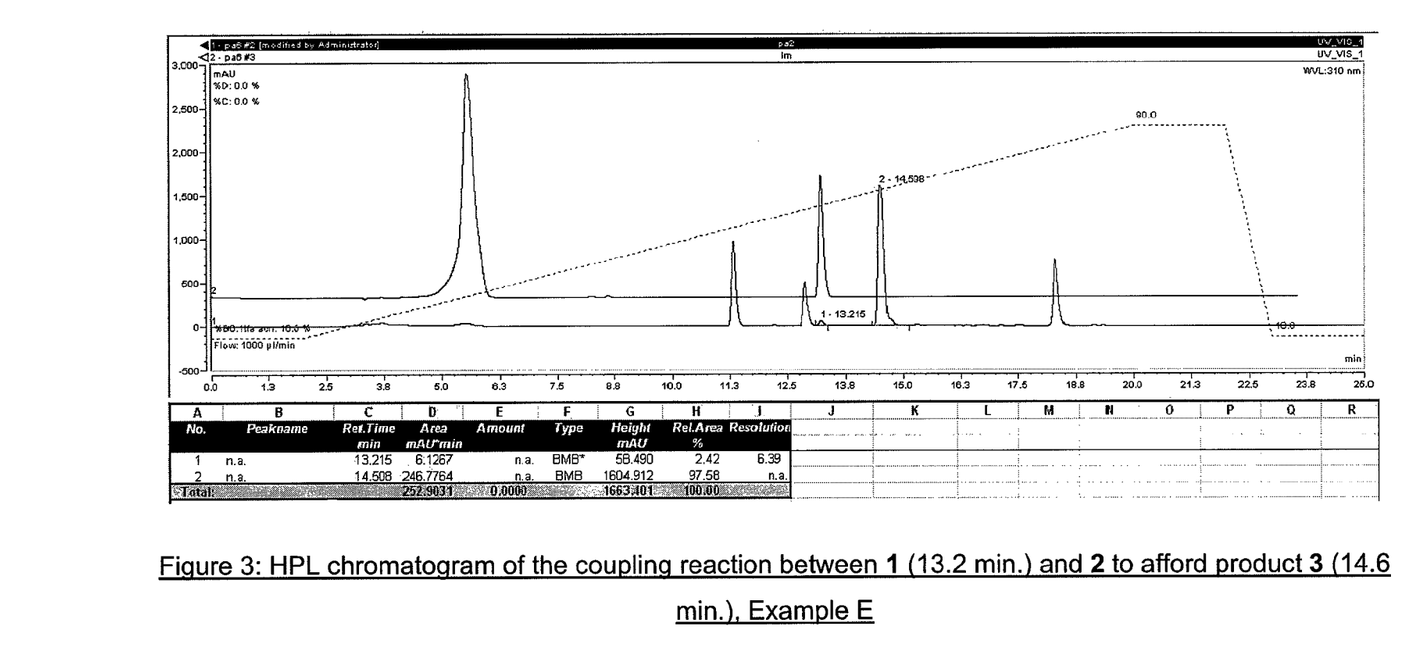
FIG. 3 is an HPL chromatogram of the coupling reaction between 1 (13.2 min.) and 2 to afford product 3 (14.6 min.) as produced in Example E.

The reaction was then quenched with diethyl ether (1 mL) and the resulting precipitate was isolated by centrifugation. Referring to FIG. 3, analysis by reverse phase HPLC indicated a 97.6% conversion to the desired coupled product (3, 14.6 min; 1, 13.2 min). Thus, the inventor has clearly demonstrated that the methods of the invention can be solution based.

The invention claimed is:

1. A process for the preparation of an amide linkage between an amine and a carboxylic acid of an amino-protected amino acid, which comprises a coupling reaction of an amine with an amino acid of formula I, PG$^1$-HN-A$^1$-COOH      I wherein:
A$^1$ represents an optionally substituted aromatic moiety;
PG$^1$ represents an amino protecting group of the formula —C(O)OR$^1$; and
R$^1$ represents a secondary or tertiary C$_{3-8}$ alkyl group,
wherein the reaction is performed in the presence of diphosgene and/or triphosgene.

2. A process for the preparation of a polyamide of formula IG,

X$^1$—(—HN-A$^1$-CO—)$_n$NH—B$^1$      IG wherein: B$^1$ represents an optionally substituted aliphatic or aromatic moiety;
X$^1$ represents —PG$^1$, —H (if any protecting group has been removed), or —C(O)A$^1$;
n represents an integer of two or more; and
PG$^1$ and each A$^1$ are as defined in claim 1;
wherein the process comprises the process of claim 1.

3. The process for preparing a compound of formula IG as claimed in claim 2, wherein in a first step, a compound of formula II, H$_2$N—B$^1$      II is reacted with a compound of formula I as defined in claim 1, and in a subsequent step the deprotected amine so formed is further reacted with another compound of formula I, the latter step being repeated until the desired number of monomer units in the compound of formula IG is attained, wherein each step is performed in accordance with the process of claim 1.

4. The process of claim 1, wherein the process is carried out as solution phase synthesis.

5. The process of claim 1, wherein the process is carried out as solid phase synthesis.

6. The process of claim 2, wherein B$^1$ is attached to a resin, thereby making the process amenable to solid phase synthesis.

7. The process of claim 1, wherein each A$^1$ independently represents one of the following substructures:

8. The process of claim 2, wherein B$^1$ represents —C(O)—CH$_2$—CH$_2$—NH$_2$.

9. The process of claim 1, wherein the process is performed in the presence of triphosgene.

10. The process of claim 1, wherein the process is performed below about 50° C.

11. The process of claim 1, wherein the coupling reaction is automated.

12. The process of claim 1, wherein the process is for the production of a polyamide, such as a straight-chain polyamide, a cyclic amide, or a hairpin polyamide.

13. The process of claim 1, wherein the amino acid of formula I comprises a natural amino acid residue or a non-natural amino acid residue.

14. The process of claim 10, wherein the process is performed below about 30° C.

15. The process of claim 10, wherein the process is performed at about 20 to 25° C.

16. The process of claim 13, wherein the amino acid of formula I is a non-natural amino acid residue.

* * * * *